(12) United States Patent
Ehrnsperger et al.

(10) Patent No.: US 6,727,403 B1
(45) Date of Patent: Apr. 27, 2004

(54) ABSORBENT ARTICLE EXHIBITING HIGH SUSTAINED ACQUISITION RATES

(75) Inventors: Bruno Johannes Ehrnsperger, Frankfurt (DE); Georgious Poursanidis, Frankfurt (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,167

(22) PCT Filed: Jun. 29, 1999

(86) PCT No.: PCT/US99/14649

§ 371 (c)(1),
(2), (4) Date: Dec. 20, 2000

(87) PCT Pub. No.: WO00/00142

PCT Pub. Date: Jan. 6, 2000

(30) Foreign Application Priority Data

| Jun. 29, 1998 | (WO) | ............................................. 98/13449 |
| Jun. 29, 1998 | (WO) | ............................................. 98/13497 |
| Jun. 29, 1998 | (WO) | ............................................. 98/13521 |
| Jun. 29, 1998 | (WO) | ............................................. 98/13523 |

(51) Int. Cl.$^7$ ................................................. A61F 13/15

(52) U.S. Cl. .................. 604/378; 604/378; 604/385.01; 604/358; 604/385.23; 604/385.101

(58) Field of Search ............................ 604/378, 385.01, 604/358, 385.23, 385.101

(56) References Cited

U.S. PATENT DOCUMENTS 5,294,478 A     3/1994  Wanek et al.

FOREIGN PATENT DOCUMENTS

| WO | WO 97/23182    | 7/1997 |
| WO | WO 97/34559 A1 | 9/1997 |
| WO | WO 98/22065    | 5/1998 |
| WO | WO 98/22066    | 5/1998 |
| WO | WO 98/22068    | 5/1998 |

*Primary Examiner*—Aaron J. Lewis
*Assistant Examiner*—Jaqueline Stephens
(74) *Attorney, Agent, or Firm*—Ian S. Robinson; Matthew P. Fitzpatrick; Ken K. Patel

(57) ABSTRACT

The present invention provides an absorbent structure to be used in an absorbent article such as a diaper, a training pant, an adult incontinence absorbent article, a bed mat, or the like, and the respective absorbent article. The absorbent structure of the present invention is able to rapidly acquire urine even against gravity as is quantified by the liquid drip off test defined herein.

10 Claims, No Drawings

ABSORBENT ARTICLE EXHIBITING HIGH SUSTAINED ACQUISITION RATES

FIELD OF THE INVENTION

The present invention relates to absorbent articles for handling urine such as diapers, training pants, adult incontinence absorbent articles, bed mats, and the like. In particular, the present invention relates to those absorbent articles which store urine by means of either capillary or osmotic pressure.

BACKGROUND

Absorbent articles such as diapers, training pants, adult incontinence absorbent articles, bed mats, and the like are well known in the art and are frequently used for example for babies, toddlers, incontinent persons, and bed-ridden persons.

For many of the intended use conditions, it is desirable for these absorbent articles to exhibit sustained high acquisition rates. For example, in the field of baby diapers it is desired to acquire the discharged urine at a high rate, most preferably with the speed the urine is discharged from the body. This high absorption rate guarantees that all of the discharged urine is actually acquired into the absorbent article. Otherwise, urine which is not readily acquired may move on the surface of the absorbent article and on the skin leading to prolonged skin contact with urine. In addition, urine not acquired by the absorbent article may run off and result in leakage from the absorbent article.

There are certain usage conditions which require a particularly good acquisition performance of the absorbent article. Frequently, urine is discharged from the body in a direction which is different from the direction of gravity. When such urine comes into contact with an absorbent article, the absorbent article is required to acquire that urine against gravity. For example, when the user of the absorbent article lies on his back the direction of urine discharge is anywhere between horizontal and upwards. Hence, urine which is not immediately acquired into the absorbent article will either drip off from the absorbent article or run down the absorbent article and cause the above problems.

Apparently, the higher the rate of urine acquisition by the absorbent article is the less urine may run off from the topsheet of the absorbent article. More preferably, the liquid acquisition rate of the absorbent article is at least at the 50 percentile of urination speed of the intended uses of the absorbent article. Most preferably, the liquid acquisition rate is at least at the 95 percentile of the intended uses of the absorbent article.

In addition, it is desirable for such absorbent articles to exhibit such high liquid absorption rates even for a plurality of subsequent gushes. For example, in the field of baby diapers the typical usage time span on average covers about four liquid gushes. Of course, it is then desired that the absorbent article also absorbs the fourth gush at a sufficiently high rate.

It is further important that the liquid is acquired by the absorbent article and held with sufficient force to not run out of the absorbent article again. This means that the absorbent article must be able to immediately store the acquired liquid in case it is not directly absorbed by the ultimate storage material.

In the prior art, many of the absorbent articles have not being able to provide sufficiently high absorption rates, and in particular have not been able to provide to absorption rates in the range of urine discharge ranges of the body. Hence, the discharged urine either stayed on the topsheet of the absorbent article thereby causing prolonged skin contact with the liquid or was running off the topsheet of the absorbent article thereby resulting in leakage.

Hence, it is an object of the present invention to provide an absorbent article which overcomes the problems posed by the prior art absorbent articles.

It is a further object of the present invention to provide the absorbent article which exhibits a low liquid drip off in the first gush and preferably also in the fourth gush.

It is a further object of the present invention to provide an absorbent article which exhibits sustained high absorption rates in the first gush and preferably also in subsequent gushes up to the fourth gush.

SUMMARY OF THE INVENTION

The present invention provides an absorbent structure comprising a first member for liquid acquisition and liquid distribution and a second member for ultimate storage of the acquired liquid. The absorbent structure of the present invention article has a liquid drip off ratio of less than 50 percent in the fourth gush of 75 ml at 15 ml/s according to the liquid drip off test defined herein. Alternatively, the absorbent structure of the present invention has a liquid drip off ratio of less than 4 percent in the first gush of 75 ml at 15 ml/s according to the liquid drip off test defined herein. Alternatively, the absorbent structure has a liquid drip off ratio of less than 60 percent in the third gush of 110 ml at 22 ml/s according to the liquid drip off test defined herein. Alternatively, the absorbent structure has a liquid drip off ratio of less than 4 percent in the first gush of 110 ml at 22 ml/s according to the liquid drip off test defined herein.

The present invention further provides an absorbent article comprising an absorbent structure according to the present invention.

DETAILED DESCRIPTION OF THE INVENTION

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

The present invention provides absorbent structure to be used in absorbent articles such as for example baby diapers, training pants, adult incontinence absorbent articles, bed mats, and the like. The present invention further provides the respective absorbent articles.

The term "handling urine" includes but is not limited to acquiring, distributing, and storing urine.

The present invention provides an absorbent structure comprises a first member for liquid acquisition and liquid distribution and a second member for ultimate storage of the acquired liquid. In some embodiments, a unitary member may serve a first member and as a second member in the absorbent structure of the present invention.

The absorbent structure of the present invention is able to acquire urine against gravity. Under many in use conditions, the direction of gravity is substantially different from being perpendicular to the surface of the absorbent structure through which urine is to be acquired into the absorbent structure. In other words, the urine is pulled away from the direction of optimum liquid acquisition into the absorbent structure by the gravitational forces. To readily acquire urine under in-use conditions, the absorbent structure must not solely relying on gravitational forces for liquid acquisition. Preferably, the absorbent structure of the present invention is able to acquire urine against gravity at least at the average rate with which urine is discharged from the body of the intended user. More preferably, the absorbent structure of the present invention is able to acquire urine against gravity at least at the 95 percentile of the urine discharge rate of the intended user.

The term "urine discharge rate" as used herein refers to the rate at which urine is discharged from the respective urethra of the wearer. The urine discharged rate varies substantially for the different usage contexts. For example in the baby diaper context, it is known that urine is discharged from the toddler's urethra on average at a rate of up to 15 milliliters per second. The 95 percentile of the toddler's urine discharge rate is 22 milliliters per second. It is further known that urination rates of up to 40 ml/s can be found at adult incontinent persons.

For the purposes of the present invention, the ability to acquire urine against gravity is quantified by the liquid drip off test defined hereinafter. The liquid drip off value in the first gush is representative of the overall liquid drip off performance of the absorbent structure, where as the liquid drip off value in the further gushes is representative of sustained low drip off performance even for subsequent gushes. The absorbent structure according to the present invention has a liquid drip off value in the first gush of 75 ml at 15 ml/s of less than 4 percent, preferably a liquid drip off value in the first gush of less than 3 percent, more preferably a liquid runoff value in the first gush of less than 2 percent, most preferably a liquid drip off value of less than 1 percent. Optionally, the absorbent structure of the present invention has a liquid drip off value in the second gush of 75 ml at 15 ml/s of less than 20 percent, preferably of less than 15 percent, more preferably of less than 10 percent, most preferably of less than 5 percent. Optionally, the absorbent structure of the present invention has a liquid drip off value in the third gush of 75 ml at 15 ml/s of less than 40 percent, preferably of less than 20 percent, more preferably of less than 10 percent, most preferably of less than 5 percent. Optionally, the absorbent structure of the present invention has a liquid drip off value in the fourth gush of 75 ml at 15 ml/s of less than 50 percent, preferably of less than 25 percent, more preferably of less than 10 percent, most preferably of less than 5 percent. Optionally, the absorbent structure according to the present invention has a liquid drip off value in the first gush of 110 ml at 22 ml/s of less than 4 percent, preferably a liquid drip off value in the first gush of less than 3 percent, more preferably a liquid runoff value in the first gush of less than 2 percent, most preferably a liquid drip off value of less than 1 percent. Optionally, the absorbent structure of the present invention has a liquid drip off value in the second gush of 110 ml at 22 ml/s of less than 20 percent, preferably of less than 15 percent, more preferably of less than 10 percent, most preferably of less than 5 percent. Optionally, the absorbent structure of the present invention has a liquid drip off value in the third gush of 110 ml at 22 ml/s of less than 40 percent, preferably of less than 20 percent, more preferably of less than 10 percent, most preferably of less than 5 percent. Optionally, the absorbent structure of the present invention has a liquid drip off value in the fourth gush of 110 ml at 22 ml/s of less than 60 percent, preferably of less than 30 percent, more preferably of less than 15 percent, most preferably of less than 5 percent.

Conventional absorbent structures such as those used in conventional absorbent articles have been found to exhibit much higher liquid drip off value for all above gushes numbers, all above gush sizes, and all above gush rates.

The absorbent article of the present invention exhibits a high acquisition rate. In particular, the absorbent article exhibits a high sustained acquisition rate, i.e. the high acquisition rate even for a plurality of subsequent gushes. High absorption rates are desired for manifold reasons. Fast acquisition of the liquid into the absorbent article ensures a short skin contact time with the urine. Prolonged skin contact with liquids such as urine may result in overhydrated skin and even in dermatitis. Furthermore, urine that is not readily acquired into the absorbent article may run off of the surface of the absorbent article and may in turn cause leakage of the urine.

For the purposes of the present invention, the liquid acquisition rates of the absorbent article of the present invention are quantified by the curved acquisition test disclosed hereinafter. The absorbent article according to the present invention has a liquid acquisition rate in the first gush of at least 5 milliliters per second, preferably a liquid acquisition rates in the first gush of at least 10 milliliters per second, more preferably a liquid acquisition rate and the first gush of at least 15 milliliters per second, most preferably a liquid acquisition rate in the first gush of at least 22 milliliters per second. Alternatively the absorbent article according to the present invention has a liquid acquisition rate in the fourth gush of at least 2 milliliters per second, preferably a liquid acquisition rate in the fourth gush of at least 5 milliliters per second, more preferably a liquid acquisition rate in the fourth gush of at least 10 milliliters per second, most preferably a liquid acquisition rate in the fourth gush of at least 15 milliliters per second.

The absorbent article according to the present invention has a z-direction. The term "z—direction" as used herein refers to the direction which is perpendicular to the surface of the absorbent article in the vicinity of the intended loading point. The z—direction is also referred to as the caliper of the absorbent article. It is desirable for the absorbent article according the present invention to have a loading point z—direction which is as small as possible in order to not exhibit high bulk between the legs of the wearer.

Preferably, the absorbent article according to the present invention has a loading point z—direction of less than 30 mm, more preferably of less than 20 mm, most preferably of less than 15 mm.

The absorbent article according to the present invention has a y—direction. The term "y—direction" as used herein refers to the direction which is tensioned to the surface of the absorbent article in the vicinity of the loading point and which is perpendicular to the longitudinal dimension of the absorbent article. It is desirable for the absorbent article according to the present invention to have a loading point y—direction which is as small as possible in order to not exhibit high above it necks of the wearer.

Preferably, the absorbent article according to the present invention has a loading point y—direction of less than 100 milliliters, more preferably of less than 80 milliliters, most preferably of less than 60 mm.

It is another aspect of the present invention to provide an absorbent structure and the respective absorbent article which comprise absorbent gelling material, also known as superabsorbent material. Suitable examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

It is another aspect of the present invention to provide a liquid handling member to be used as a first member in the absorbent structure of the present invention.

In the following, a suitable embodiment of the liquid handling member will be described. The liquid handling member is assembled from an open celled foam material which is completely enveloped by a membrane. A suitable membrane material is available from SEFAR of Rüschlikon, Switzerland, under the designation SEFAR 03-20/13. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air through the membranes.

The particular geometry of the liquid handling member of the present invention can be varied to according to the specific requirements off the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood , however, that the design of the outer form of the liquid handling member may have an impact on its performance. For example, the cross section of the liquid handling member directly impacts on its flow rate.

For application of the liquid handling member in an absorbent article according to the present invention, the liquid handling member may be combined with a storage member. The term "liquid storage member" refers to an absorbent article which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. In order to pick up the liquid discharged from the liquid handling member, the storage member may be placed in direct liquid communication with the intended liquid discharge zone of the liquid handling member. A suitable storage member is for example a superabsorbent polymer such as available from CHEMDAL, United Kingdom, under the designation ASAP400.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4,1997.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entited "High flux liquid transport members comprising two different permeability regions" (P&G case CM1840MQ) filed in the name of Ehmsperger et al., "Liquid transport member for high flux rates between two port regions" (P&G case CM1841 MQ) filed in the name of Ehrnsperger et al., "Liquid transport member for high flux rates against gravity" (P&G case CM1842MQ) filed in the name of Ehrnsperger et al., "Liquid transport member having high permeability bulk regions and high bubble point pressure port regions" (P&G case CM1843MQ) filed in the name of Ehrnsperger et al. All of these documents are enclosed herein by reference.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases—a solid material and a gas or void phase—and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

In one embodiment of the present invention, the absorbent article is a disposable absorbent article such as a diaper, a training pant, a sanitary napkin, an adult incontinence absorbent article, or the like. Such an absorbent article may further comprise a liquid pervious topsheet, a liquid impervious backsheet at least partially peripherally joined to the topsheet. The absorbent article may further comprise an absorbent core which may serve as a storage member for the urine. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

METHODS

Unless stated otherwise, all tests are carried out at about 32° C.+/−2° C. and at 35+/−15% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Liquid Drip Off Test Method

The liquid drip off test aims at simulating the dispension of urine onto a absorbent article for managing urine when the wearer lies on the back. The following test is suitable for absorbent articles as a whole and it may also be used for any member or any combination of members of a absorbent article such as absorbent structure according to the present invention. This test is carried out using de-ionized water as the test liquid.

The following describes key principles of the test:
1. The test specimen is affixed to the lower surface of a support structure which forms an angle of 14 degrees with the horizontal plane.
2. The test liquid is dispensed onto the absorbent article at a urination rate representative of the intended user group.
3. Liquid that is not readily acquired into and held in the article will drip off from the absorbent article because of the sloped inverse configuration.

Similar tests for example for nonwoven materials are well known in the art such as EDANA test method 152.0—99 "nonwoven special runoff" except for the inverse configuration of the absorbent article which leads to test liquid dripping off from the test specimen rather than liquid running off from it.

The following description is adopted for absorbent articles for handling body liquids of the baby diaper type, and in particular for absorbent articles intended for babies in the weight range of about 9 to 18 kg. For these babies, the average urination rate to this 15 milliliters per second, the 95 percentile of the urination rate for the same babies is at 22 milliliters per second. Nonetheless, the skilled person will be able to readily adopt this method for other purposes, such as for other sizes, or adult incontinence applications. When there is a need for adoption of the method, the single gush volume and the delivery rate should be adjusted to better reflect the average gush volume and urination rate of a member of the intended user group. The number of gushes used in this test should be three or four depending on whether the total volume delivered by three or four gushes is closest to the total capacity of the absorbent article to be tested. The diameter of the tube and the orifice should be adjusted along with the gush size such that the linear velocity of the test liquid at the orifice remains constant.

The test specimen is held on the lower surface of a flat support structure which forms an angle of 14 degrees with a horizontal. The support structure is not absorbent and may be made from wide variety of suitable materials such as for example Plexiglas. The test specimen is affixed to the lower surface of the support surface by any suitable means which does not interfere with the liquid handling of the test specimen such as for example adhesive tapes. When the test specimen affixed to the support structure, the liquid receiving surface of the test specimen to be tested should point downwards. The configuration of the test specimen on the support structure should be as flat as possible. The test specimen is oriented such that its longitudinal dimension coincides with the slope of the support structure. The front region of the test specimen should be placed towards the upper end of the support structure where as the back region of the test specimen should be placed towards the lower end of the support structure. A liquid receptacle of adequate size is placed below the support structure in order to collect liquid dripping-off from the absorbent article.

For test specimen's having the above-mentioned size, the first test protocol loads the test specimen four times with 75 milliliters plus minus 2 milliliters of test liquid, at a rate of 15 milliliter per second, delivered at five minute intervals. Alternatively, the second test protocol loads the test specimen four times with 110 milliliters plus minus 2 milliliters of test liquid at a rate of 22 milliliters per second, delivered at five minute intervals. The present description refers to an automated procedure, including automatic data capturing. Of course, analogous systems can be used such as manual recording of data, as long as the described principles are followed.

The test liquid is dispensed from a 4.8 mm inner diameter flexible tube (outer diameter 14.4 mm), such as Tygon R-3603, available from Fisher Scientific, Germany, connected to test a liquid metering pump such as for example available from Ismatec Laboratoriumstechnik of Wertheim Mondfeld, Germany, under the designation MCP-Z Gear Pump, having a pump head available from of Ismatec Laboratoriumstechnik of Wertheim Mondfeld, Germany under the designation Micropump MOD O/C 020-000, with a pump control unit to allow start and stop of the pump based upon electrical signals. It is particularly important that the orifice has an inner diameter of 4.8 mm in order to control the velocity at which test liquid is discharged from the orifice. The tube and the orifice are configured such that the test liquid is dispensed from the tube in a direction perpendicular to the surface of the absorbent article. The orifice of the tube is positioned about 20 mm plus minus 1 mm away from the loading point of the absorbent article.

The test liquid dripping off from the test specimen is collected in the liquid receptacle placed below the support structure. The receptacle is dimensioned such that all of the test liquid dripping off from the test specimen is collected. The amount of test liquid received by the receptacle is determined by the weight increase of the receptacle during the test procedure. The weight increase of the liquid receptacle is measured with digital balance having an accuracy of 10 micrograms.

Upon finishing of the above 4 liquid dispension cycles, the liquid drip-off for each of the gushes has been obtained. The liquid drip-off for each of the gushes is reported as the percentage of the total volume of a respective single gush that has dripped off from the surface into the receptacle.

Curved Acquisition Test Method

The curved acquisition test method aims at simulating the introduction of urine into a absorbent article for managing body liquids. A similar test method is described in PCT patent application No. IB99100741 (P&G case CM2060FQ) incorporated herein by reference.

The following describes key principles of the test:
1. The absorbent article is held in a curved configuration to more realistically simulate the position of the absorbent article on a standing or sitting wearer.
2. The realistic, curved configuration requires that the liquid applied must be distributed against gravity.
3. The overall configuration provides key data on acquisition, distribution and storage of the liquid within the various materials thereby providing a better understanding of material properties, and their combined performance.
4. The apparatus includes a pressurized air cushion, allowing to better analyze products which have either a varying thickness throughout various parts thereof, or which exhibit a pronounced thickness change throughout the loading process.

The following description is adopted for absorbent articles for handling body liquids of the baby diaper type, and in particular for absorbent articles intended for babies in a weight range of about 9 to 18 kg. Nonetheless, the skilled person will be able to readily adopt it for other purposes, such as for other sizes, or adult incontinence applications. The test specimen is held in a curved plexiglas absorbent article which utilizes a flexible, soft air bag which is used to simulate-various baby pressures between 0.69 kPa–6.9 kPa (0.1–1 psi), and the test specimen is loaded with subsequent gushes of liquid, with appropriate waiting time in between. The key result from this test is the time for the fluid of each of the gushes to penetrate into the test specimen. After the loading of the test specimen by this test, the test specimen can be used for further analysis, such as measuring the rewet, preferably by the Post Curved Acquisition Collagen Rewet Method (PCACORM) described in PCT patent application IB99/00741 (P&G case CM2060FQ), or measuring the caliper, or measuring the liquid distribution, such as by determining the load in various sections of the test specimen.

For test specimens having the above mentioned size, the standard protocol loads the test specimen four times with 75 ml+/−2 ml, at a rate of 15 ml/sec, delivered at 5 minute intervals. The present description refers to an automated procedure, including automatic data capturing. Of course, analogous systems can be used, such as manual recording of data, as long as the described principles are followed.

The test equipment is schematically depicted in FIG. 6 of PCT patent application No. IB99/00741 (P&G case CM2060FQ) incorporated herein by reference. The complete equipment, or preferably a multiplicity thereof for ease of replication, is placed inside a controlled condition chamber, with room temperature and humidity within the following limits:

Temperature: 32° C.±2° (90° F.±3° F.)

Relative Humidity: 50%±10%

If a deviation from this protocol is deemed appropriate, this must be stated explicitly in the protocol.

The Curved Acquisition Tester comprises four important parts (The size of this unit is designed for baby diapers. Accordingly, the size may need to be adopted for absorbent article intended for different user groups):

a) A holding unit which is essentially made of perspex/plexiglas. It has been found that suitable plates of 5 mm thickness provide sufficient strength for operating without undue deformation.

The essential part of the holding unit is a trough having an upper rectangular opening of 130 mm extending outside of the plane of drawing, and a width of 260 mm. The rectangular through has a length of about 200 mm and ends in a semi-cylindrical form having a radius of 130 mm. The holding unit has one or more means to retain the loading unit in place, here shown by a hinged lid and corresponding fixation means, such as screws. The holding unit further comprises means for stable support.

b) A loading unit comprising a liquid application means is designed to fit into the through of the holding unit, by having a rectangular section having a length of about 180 mm, and having cross-section of about 100 mm by 128 mm, ending in a semi-cylindrical section having a radius of 100 mm. The loading unit further comprises a flange, which allows to hang the unit into the trough by being larger than said trough opening, and which also prevents the loading unit to be pushed out of the trough by being hold by said lid. The clearance for the vertical movement of the loading unit is about 4 cm. The total loading unit is made from the same material as the holding unit, and can have a weight of about 1 kg, including the liquid application means.

c) The liquid application means comprises a plexiglas tube having an inner diameter of 47 mm, and a height of about 100 mm. It is firmly affixed to a circular opening having a diameter of about 50 mm through the loading unit, positioned centered around the lowermost point of the semi-cylindrical portion. The opening of the tube is covered by a open mesh (such as of wire mesh with openings of about 2 mm separated by threads of 1 mm), so as to be flush with the opening of the loading unit. A 6 mm diameter flexible tube, such as Norpren A60G (6404-17), available from Cole Parmer Instrument Company, IL, US, is connected to a test fluid metering pump, such as Digital Pump, Catalog, by No. G-07523-20, having a Easy-Load Pump Head, No. G-07518-02, both by Cole-Parmer Instrument Company, IL, US, with a pump control unit to allow start and stop of the pump based upon electrical signals. Two electrodes are positioned at two opposite points just inside the mesh at the lower end of the plexiglas tubing, to be able to detect interruption of the electric current through the electrolyte fluid, once the tube is being emptied. The electrodes are connected via cable to a time signal measuring unit.

d) A pressure generating means comprises a flat, flexible air cushion, such as generally available for medical purposes (blood pressure measurement), having an uninflated dimension of 130 mm by 600 mm, which can be inflated by means of a hand pump and a valve with a pressure recording absorbent article, which can be connecting to an electrical transducer so as to provide an electrically recordable signal corresponding to the pressure.

This system is designed to operate at pressures of up to 6.89 kPa (1 psi), and is set for the standard procedure to 2.07 kPa (0.3 psi).

e) Optionally, the apparatus can comprise an automatic control unit, such as a suitable computer control unit, connected to the pump control unit, the timer and the pressure recorder which also can operate several measuring units in parallel. Suitable software is for example LabView ® by National Instruments, Munich, Germany. A complete test equipment can be delivered by High Tech Company, Ratingen/Germany, D-64293 Darmstadt.

Steps for Setting up the Acquisition Equipment

1) Calibration of pump: before starting the experiment, the pump should be calibrated to ensure a flow rate of 75 ml per 5 seconds. If necessary, tubing should be replaced.
2) Preparation and thermal equilibration of test fluid;
3) Positioning of the cushion into the trough without folds or creases;
4) Weighing of the entire absorbent article to be tested to the nearest 0.01 g on a top loading balance. Marking of the loading point onto the test specimen with a pen. Positioning and fixation (such as by suitable adhesive tape) of the test specimen to the loading unit, such that the liquid receiving surface is oriented towards the loading unit (and hence the backsheet towards the cushion), so as to have the opening aligned with the loading point of the absorbent article. The absorbent article is then positioned onto the curved loading unit without cutting the leg elastics or other elastic, if present, with the marked loading point located under the center of the tube, and attached to the loading unit by suitable attachment means, such as tape. Generally, the configuration of the absorbent article should resemble a typical in use configuration as close as possible. The absorbent article is then positioned together with the loading unit into the tester, and the electrode cables are connected.
5) The lid is closed, and fixed with screws.
6) The cushion is then inflated to the desired pressure, i.e. 2.07 kPa (0.3 psi), thereby pushing the loading unit against the lid, and thus exerting the pressure on the test specimen.
7) The end of the flexible tube is positioned such that it directs to the center of the opening, and extends about 5 cm (2 in) into the tube.
8) The liquid pump is started for the preset time (i.e. 5 seconds), and at the same time acquisition time timer.
9) Upon emptying of the Plexiglas tube the electrodes provide a signal stopping the acquisition time timer, upon which the waiting time is started at the timer for 5 minutes.
10) The loading cycle (step 7 and 8) is repeated to a total of four times.

Results

Upon finishing of the above cycle, the respective acquisition rates can be calculated for each "gush" by dividing the load per gush (i.e. 75 ml) by the time in seconds required for each gush. (if the acquisition rates are getting close to the liquid delivery rates (i.e. 15 ml/sec), test conditions can be changed and respectively recorded.)

What is claimed is:

1. An absorbent structure comprising a first member for liquid acquisition and liquid distribution, a second member for ultimate storage of acquired liquid, wherein said absorbent structure has a liquid drip off ratio of less than 50 percent in a fourth gush of 75 ml at 15 ml/s.

2. An absorbent structure comprising a first member for liquid acquisition and liquid distribution, a second member for ultimate storage of acquired liquid by means of capillary or osmotic pressure wherein said absorbent structure has a liquid drip off ratio of less than 4 percent in a first gush of 75 ml at 15 ml/s.

3. An absorbent structure comprising a first member for liquid acquisition and liquid distribution, a second member for ultimate storage of acquired liquid wherein said absorbent structure has a liquid drip off ratio of less than 60 percent in a third gush of 110 ml at 22 ml/s.

4. An absorbent structure comprising a first member for liquid acquisition and liquid distribution, a second member for ultimate storage of acquired liquid wherein said absorbent structure has a liquid drip off ratio of less than 4 percent in a first gush of 110 ml at 22 ml/s.

5. An absorbent structure according to claim 1 wherein said second member stores liquid by means selected from the group consisting of capillary forces and osmotic forces.

6. An absorbent structure according to claim 5, wherein said second member comprises an absorbent gelling material.

7. An absorbent article comprising an absorbent structure according to claim 1, wherein said absorbent structure has an acquisition rate of a first gush of at least 5 milliliters per second.

8. An absorbent article comprising an absorbent structure according to claim 1, wherein said absorbent structure has an acquisition rate of a fourth gush of at least 2 milliliters per second according.

9. An absorbent article comprising an absorbent structure according to claim 1 wherein said absorbent article is a disposable absorbent article.

10. An absorbent article according to claim 9, wherein said absorbent article is a disposable diaper.

* * * * *

UNITED STATES PATENT AND TRADEMARK OFFICE
CERTIFICATE OF CORRECTION

PATENT NO. : 6,727,403 B1  
DATED : April 27, 2004  
INVENTOR(S) : Bruno Johannes Ehrnsperger, Georgios Poursanidis and Mattias Schmidt It is certified that error appears in the above-identified patent and that said Letters Patent is hereby corrected as shown below:

<u>Title page,</u>
Item [75], Inventors, delete "Georgious Poursanidis" and
insert -- Georgios Poursanidis --

Signed and Sealed this

Sixth Day of July, 2004

JON W. DUDAS
*Acting Director of the United States Patent and Trademark Office*